(12) United States Patent
Srinivasan et al.

(10) Patent No.: US 11,071,833 B2
(45) Date of Patent: Jul. 27, 2021

(54) PEN NEEDLE MAGAZINE

(71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 263 days.

(21) Appl. No.: 16/094,809

(22) PCT Filed: Mar. 31, 2017

(86) PCT No.: PCT/US2017/025287
§ 371 (c)(1),
(2) Date: Oct. 18, 2018

(87) PCT Pub. No.: WO2017/189165
PCT Pub. Date: Nov. 2, 2017

(65) Prior Publication Data
US 2019/0117904 A1    Apr. 25, 2019

Related U.S. Application Data

(60) Provisional application No. 62/328,660, filed on Apr. 28, 2016.

(51) Int. Cl.
*A61M 5/32* (2006.01)
*A61M 5/34* (2006.01)
(Continued)

(52) U.S. Cl.
CPC .......... *A61M 5/3293* (2013.01); *A61M 5/002* (2013.01); *A61M 5/24* (2013.01);
(Continued)

(58) Field of Classification Search
CPC ........ A61M 5/24; A61M 5/32; A61M 5/3202; A61M 5/3297; A61M 5/3298;
(Continued)

(56) References Cited

U.S. PATENT DOCUMENTS 5,829,589 A   11/1998  Nguyen et al.
5,873,462 A    2/1999  Nguyen et al.
(Continued)

FOREIGN PATENT DOCUMENTS

EP    2119423 A1   11/2009
EP    2420270 A2    2/2012
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Bhisma Mehta
*Assistant Examiner* — John J Crawford
(74) *Attorney, Agent, or Firm* — Dickinson Wright PLLC

(57) ABSTRACT

An attachable needle assembly (2) for use on a medication delivery pen (4), the needle assembly (2) comprising a housing (10) enclosing a spike housing (8) configured to (a) engage the medication delivery pen (4), and (b) pierce a reservoir septum (6) of the medication delivery pen (4), a communication septum (72, 76) of the needle assembly (2) defining a septum chamber (80, 82), the septum chamber (80, 82) being in fluid communication with the spike housing (8), a plurality of needles (18) disposed in the commu- (Continued)

nication septum (72, 76), a selection ring insert (30) that rotates and identifies a needle (24) of the plurality of needles (18), and a selection ring (36) exposes the selected needle (24) and moves the selected needle (24) into fluid communication with the septum chamber (80, 82), wherein when the housing (10) is in a first position, the plurality of needles (18) is not exposed, and when the housing (10) is in a second position, one of the plurality of needles (24) is in fluid communication with the septum chamber (80, 82) and exposed for medicament delivery.

26 Claims, 13 Drawing Sheets

(51) Int. Cl.
    *A61M 5/24*        (2006.01)
    *A61M 5/00*        (2006.01)
(52) U.S. Cl.
    CPC ............ *A61M 5/32* (2013.01); *A61M 5/3202* (2013.01); *A61M 5/3297* (2013.01); *A61M 5/34* (2013.01); *A61M 5/3298* (2013.01); *A61M 2005/004* (2013.01); *A61M 2005/2474* (2013.01); *A61M 2205/18* (2013.01)
(58) Field of Classification Search
    CPC ................. A61M 5/3293; A61M 5/34; A61M 2005/004; A61M 2205/18; A61M 5/002; A61M 5/3295
    See application file for complete search history.

(56) References Cited

U.S. PATENT DOCUMENTS

| | | |
|---|---|---|
| 5,931,817 A | 8/1999 | Nguyen et al. |
| 8,876,780 B2 | 11/2014 | Bruehwiler et al. |
| 9,101,724 B2 | 8/2015 | Chapin et al. |
| 9,107,988 B2 | 8/2015 | Bruehwiler et al. |
| 9,155,838 B2 | 10/2015 | Bilton et al. |
| 9,381,303 B2 | 7/2016 | Abhijitsinh et al. |
| 9,717,860 B2 | 8/2017 | Bruehwiler et al. |
| 10,029,042 B2 | 7/2018 | Searle et al. |
| 2001/0014792 A1 | 8/2001 | West et al. |
| 2002/0020646 A1 | 2/2002 | Groth et al. |
| 2002/0020647 A1 | 2/2002 | Groth |
| 2005/0084631 A1 | 4/2005 | Anderson |
| 2008/0312604 A1 | 12/2008 | Boesen |
| 2010/0217206 A1 | 8/2010 | Lum et al. |
| 2011/0068034 A1 | 3/2011 | Hwang et al. |
| 2012/0004620 A1 | 1/2012 | Spool et al. |
| 2012/0016315 A1 | 1/2012 | Radmer et al. |
| 2012/0041373 A1* | 2/2012 | Bruehwiler ........... A61M 5/002 604/173 |
| 2012/0041381 A1 | 2/2012 | Raj et al. |
| 2012/0041383 A1 | 2/2012 | Bruehwiler et al. |
| 2012/0041390 A1 | 2/2012 | Spool et al. |
| 2013/0041321 A1 | 2/2013 | Cross et al. |
| 2013/0053751 A1 | 2/2013 | Holtham |
| 2014/0076758 A1 | 3/2014 | Dasbach et al. |
| 2014/0123479 A1 | 5/2014 | Dasbach |
| 2014/0262884 A1 | 9/2014 | Priebe et al. |
| 2014/0299622 A1 | 10/2014 | Hofmann et al. |
| 2014/0332425 A1 | 11/2014 | Hofmann et al. |
| 2014/0339113 A1 | 11/2014 | Hofmann et al. |
| 2015/0025469 A1 | 1/2015 | Larsen et al. |
| 2015/0163898 A1 | 6/2015 | Mokhtarzad |
| 2015/0283333 A1 | 10/2015 | Butler et al. |
| 2015/0335827 A1 | 11/2015 | Stefansen et al. |
| 2015/0346184 A1 | 12/2015 | Galasso |
| 2016/0000992 A1 | 1/2016 | Steel et al. |
| 2016/0030683 A1 | 2/2016 | Taylor et al. |
| 2016/0074587 A1 | 3/2016 | Searle et al. |
| 2016/0082195 A1 | 3/2016 | Atterbury et al. |
| 2016/0106925 A1 | 4/2016 | Boesen |

FOREIGN PATENT DOCUMENTS

| | | |
|---|---|---|
| EP | 2428236 A1 | 3/2012 |
| EP | 2586475 A1 | 5/2013 |
| EP | 2604304 A1 | 6/2013 |
| EP | 2696913 B1 | 9/2015 |
| WO | 2008/150715 A1 | 12/2008 |
| WO | WO-2011083055 A1 | 7/2011 |
| WO | 2014/020001 A1 | 2/2014 |
| WO | 2016/050902 A1 | 4/2016 |

* cited by examiner

PEN NEEDLE MAGAZINE

This application claims the benefit under 35 U.S.C. § 119(e) of U.S. Provisional Patent Application Ser. 62/328,660, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a needle assembly that is attachable to a medication pen to provide a magazine of needles for use. Such a needle assembly provides advantages in separating a patient end and a non-patient end and allows for engagement and disengagement. Moreover, improvements in sterility and simplicity are achieved by the needle assembly such that none of the needles in the magazine are piercing the septum of the medication pen at any point during operation, each needle is used for injection one at a time, and each needle only moves axially.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing an attachable needle assembly for use on a medication delivery pen, the needle assembly comprising a housing enclosing a spike housing that is configured to engage the medication delivery pen, and configured to pierce a reservoir septum of the medication delivery pen, a communication septum of the needle assembly defining a septum chamber, the septum chamber of the needle assembly being in continuous fluid communication with the spike housing, a plurality of needles disposed in the communication septum of the needle assembly, a selection ring insert that rotates and identifies which needle of the plurality of needles is to be selected, and a selection ring that applies a force to expose the selected needle and moves the selected needle to be in fluid communication with the septum chamber of the communication septum of the needle assembly, wherein when the housing is in a first position, the plurality of needles is not exposed, and when the housing is in a second position, one of the plurality of needles is in fluid communication with the septum chamber of the communication septum of the needle assembly and exposed for medicament delivery.

The foregoing and/or other aspects of the present invention can also be achieved by a method of operating an attachable needle assembly for a medication delivery pen, the method comprising piercing a reservoir septum of the medication delivery pen with a spike housing, the spike housing enclosed in a housing, connecting the medication delivery pen to the spike housing, establishing fluid communication between the spike housing and a septum chamber of a communication septum of the needle assembly, disposing a plurality of needles in the communication septum of the needle assembly, rotating a selection ring insert to identify which needle of the plurality of needles is to be selected, and applying a force, by a selection ring, to the selected needle to expose the selected needle and to move the selected needle to be in fluid communication with the septum chamber of the communication septum of the needle assembly, wherein when the housing is in a first position, the plurality of needles is not exposed, and when the housing is in a second position, one of the plurality of needles is in fluid communication with the septum chamber of the communication septum of the needle assembly and exposed for medicament delivery.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
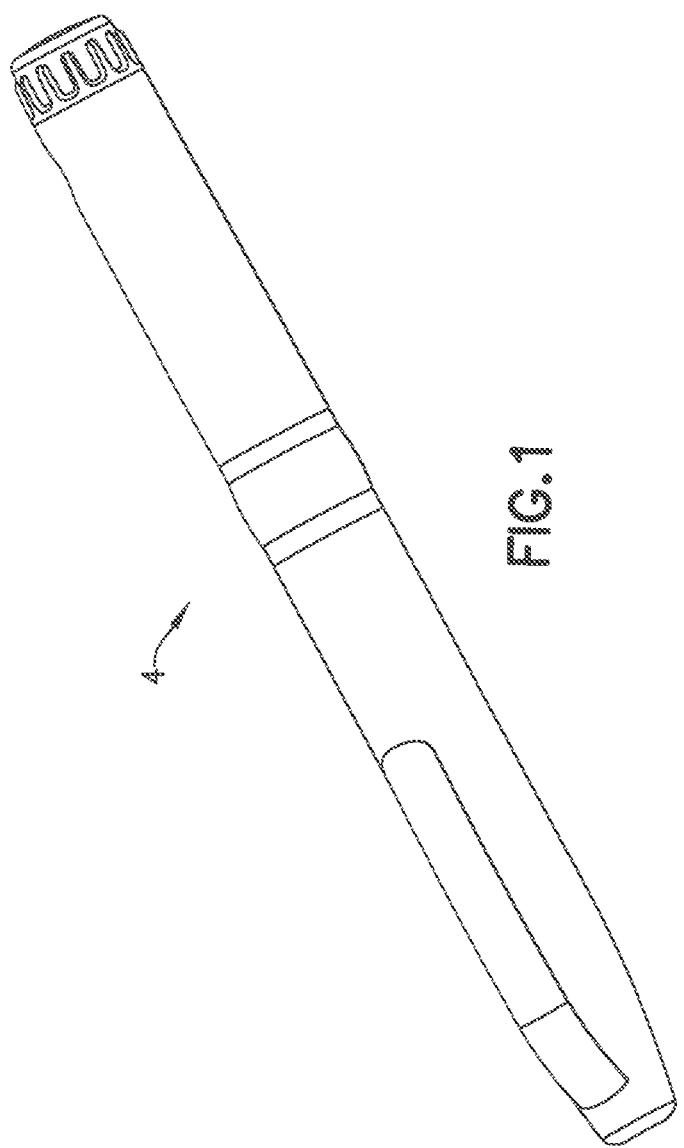
FIG. 1 illustrates a perspective view of an exemplary medication delivery pen.
Figure 2:
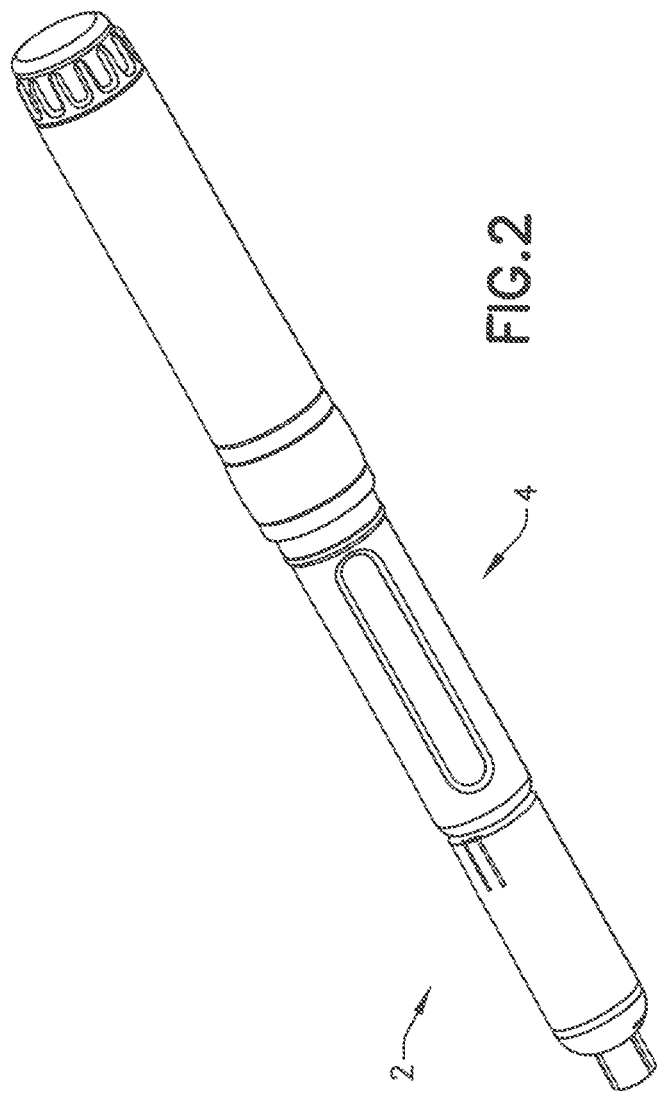
FIG. 2 illustrates a perspective view of a needle assembly attached to the medication delivery pen.

FIG. 1 illustrates a typical medication delivery pen 4 used for injecting medicament, such as liquid drugs, into a living body. FIG. 2 illustrates a needle assembly 2 mounted on the medication delivery pen 4 to enhance medication delivery. Benefits and advantages of the needle assembly 2 are described below.

Figure 3:
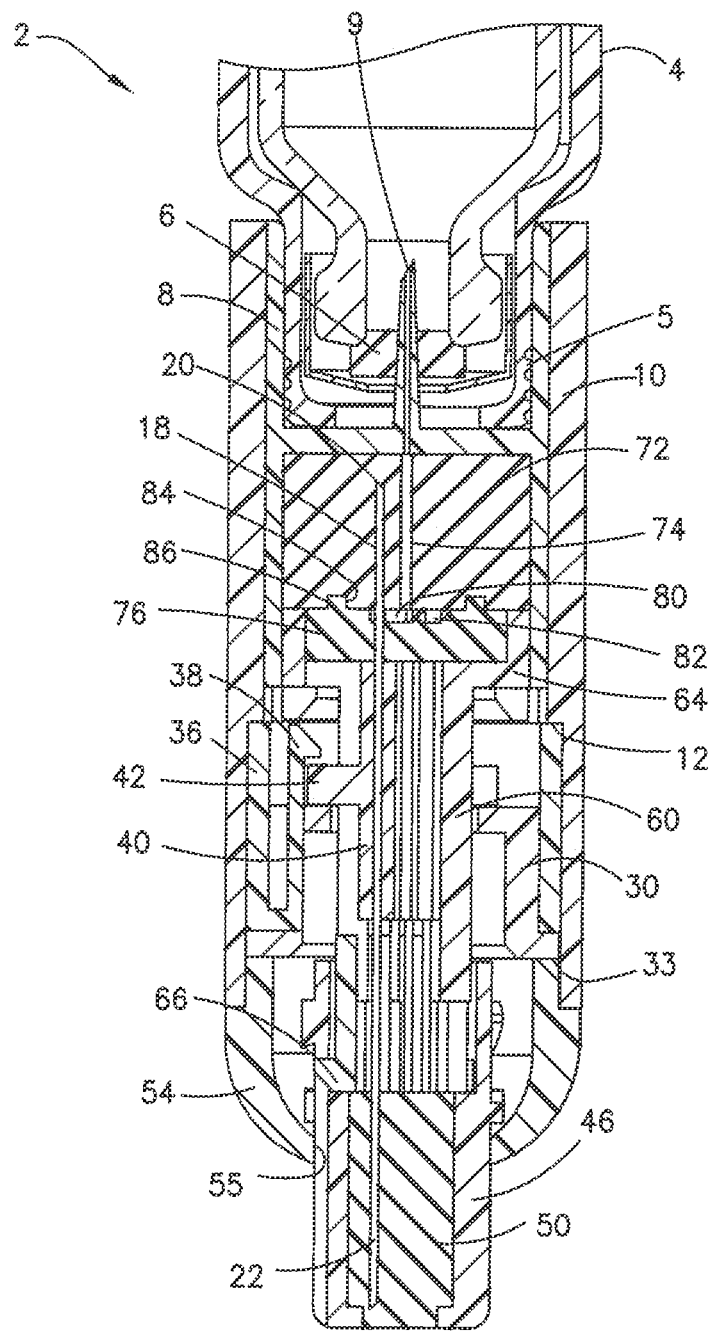
FIG. 3 illustrates a cross sectional view of the needle assembly in a first position.

According to one embodiment, FIG. 3 illustrates the needle assembly 2 mounted on the medication delivery pen 4 prior to operation in a first position. The needle assembly 2 includes a spike housing 8 having internal threads (not illustrated) that engage external threads 5 on the medication delivery pen 4. The threaded assembly allows a user to attach and detach the needle assembly 2 from the medication delivery pen 4. Although threads are disclosed, a variety of engagement mechanisms are contemplated, such as a press-fit, laser welding or the use of adhesives.

The spike housing 8 further includes a spike 9 that is configured to pierce a vial, cartridge or reservoir septum 6 of the medication delivery pen 4. When the needle assembly 2 is mounted on the medication delivery pen 4, the spike 9 pierces the reservoir septum 6 to establish fluid communication between the needle assembly 2 and the medication delivery pen 4. Specifically, the spike 9 piercing the reservoir septum 6 provides fluid communication between the needle assembly 2 and an insulin cartridge, for example, of the medication delivery pen 4.

Figure 5:
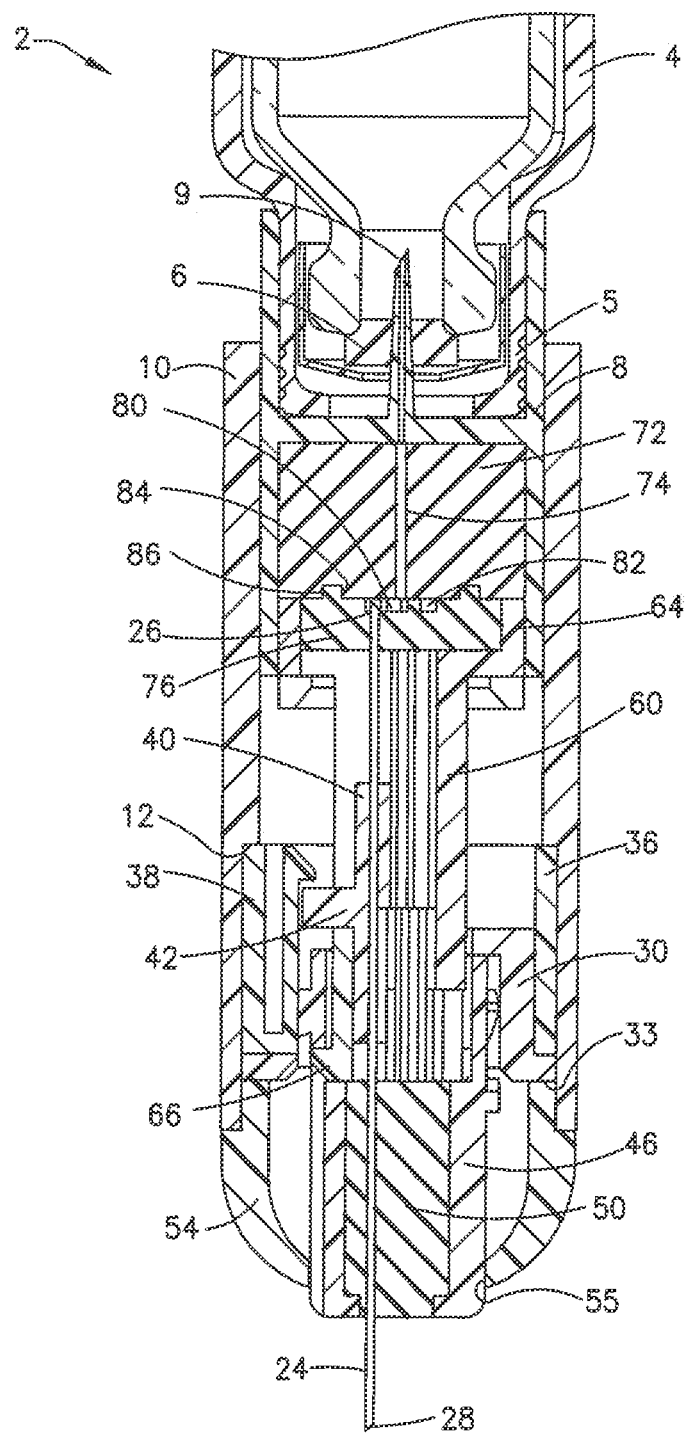
FIG. 5 illustrates a cross sectional view of the needle assembly in a second position.
Figure 9:
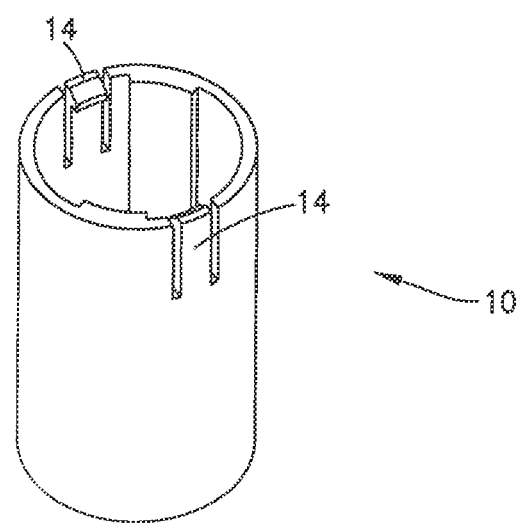
FIG. 9 illustrates a perspective view of a housing.

FIGS. 3 and 9, according to one embodiment, illustrate a housing 10 having a housing flange 14 that encloses the needle assembly 2. The housing flange 14 engages interlocks (not illustrated) of the spike housing 8 in the first position where the needle assembly 2 is not in operation. According to one embodiment, as illustrated in FIG. 5, the user moves the housing 10 to a second position where the housing flange 14 engages the interlocks (not illustrated) of the spike housing 8 to withdraw a needle 24 and operate the needle assembly 2 in fluid communication with the medication delivery pen 4. Thus, the housing 10 moves axially with respect to the spike housing 8.

The needle assembly 2 acts as a magazine for holding the plurality of hollow needles 18. Preferably, seven needles are disposed in the needle assembly 2, although more or less is contemplated. When the needle assembly 2 is mounted to the medication delivery pen 4, each of the plurality of needles 18 is disposed in a communication septum 72, 76 and a sealing septum 50 of the needle assembly 2. Specifically, a proximal end 20 of each of the plurality of needles 18 is disposed in the communication septum 72, 76 and a distal end 22 of each of the plurality of needles 18 is disposed in the sealing septum 50.

The sealing septum 50 of the needle assembly 2 aids to regulate the dispensing of medicament by sealing the plurality of needles 18 at various times during operation. The sealing septum 50 maintains a sterile environment for the plurality of needles 18 before, during and after use. After a needle is used, the sealing septum 50 encloses the distal tip and protects the distal tip from reuse and injury to the user.

Figure 4:
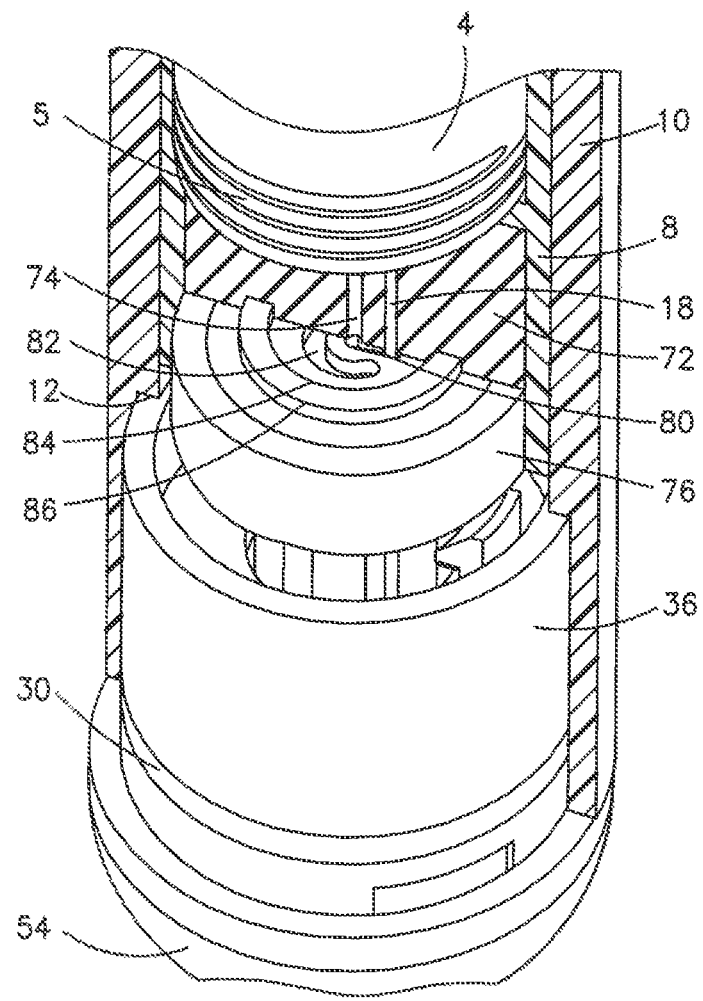
FIG. 4 illustrates a partial cross sectional view of a communication septum of the needle assembly in the first position.

According to one embodiment, the communication septum includes an upper septum 72 and a lower septum 76. The upper septum 72 is disposed within a distal end of the spike housing 8. As illustrated in FIGS. 3 and 4, the upper septum 72 includes an upper septum hole 74 that travels through the upper septum 72 at its centerline. The upper septum hole 74 communicates with the spike 9 of the spike housing 8 to allow liquid medicament to flow into the needle assembly 2.

FIGS. 3 and 4 illustrate the lower septum 76 including a septum chamber comprising a continuous circular cavity 82 and a longitudinal cavity 80. The continuous circular cavity 82 or a curved recess is disposed on a top face of the lower septum 76. The circular cavity 82 continuously extends approximately 315°±30° around the top face of the lower septum 76. At one end point of the circular cavity 82, the longitudinal cavity 80 or longitudinal recess extends toward a center of the lower septum 76. In assembly, the top face of the lower septum 76 is in direct sealing contact with a bottom face of the upper septum 72. The upper septum 72 and the lower septum 76 are preferably composed of different materials having different durometers. Such characteristics enhance sealing between the top face of the lower septum 76 and a top face of the upper septum 72. The longitudinal cavity 80 of the lower septum 76 establishes fluid communication with the upper septum hole 74 and the spike 9 to fill the septum chamber with medicament.

The lower septum 76 includes a first diameter portion 84 and a second diameter portion 86 where the first diameter portion 84 is smaller in diameter than the second diameter portion 86. Both the first and second diameter portions 84, 86 define a protrusion that mates with a corresponding recess in the bottom wall of the upper septum 72 to assemble the communication septum 72, 76. The septum chamber is disposed interior to the protrusion formed by the first and second diameter portions 84, 86.

According to one embodiment, each of the plurality of needles 18 is disposed in the communication septum 72, 76 in the first position of the needle assembly 2. Specifically, in the first position of the needle assembly 2, the proximal end 20 of each of the plurality of needles 18 is disposed in the upper septum 72 which provide needle sterility. As illustrated in FIGS. 3 and 4, the plurality of needles 18 extends through the circular cavity 82 of the lower septum 76, thus contacting the medicament. However, the plurality of needles 18 is not in fluid communication with the circular cavity 82.

In the second position of the needle assembly 2, at least one of the plurality of needles 18 is exposed for medicament delivery. Specifically, a proximal end 26 of the selected needle 24 is disposed in the circular cavity 82 of the lower septum 76 to be in fluid communication with the medicament received from the spike 9. The second position of the needle assembly 2 is described in more detail below.

When the first needle of the plurality of needles 18 is used, the circular cavity 82 is filled with medicament, resulting in the lower septum 76 being primed. Specifically, medicament must traverse and fill the complete fluid path of the circular cavity 82 to reach the first needle of the plurality of needles 18. Accordingly, the incidence of air in the circular cavity 82 is advantageously reduced. Removing air from the fluid path also advantageously improves dose accuracy.

Figure 10:
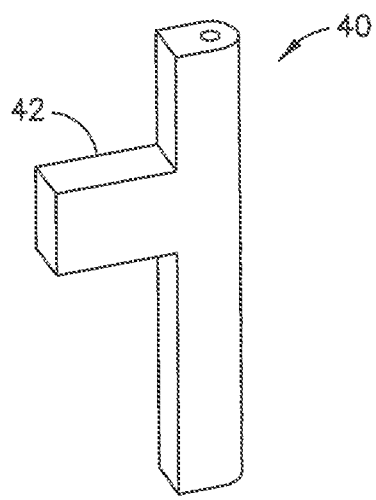
FIG. 10 illustrates a perspective view of a needle post.

According to one embodiment, each of the plurality of needles 18 is secured to a respective needle post 40, as further illustrated in FIG. 10. Each of the plurality of needles 18 is preferably secured to a needle post 40 by an adhesive, such as a medical grade adhesive, but other adhesives and other fastening means such a press fit is contemplated. The adhesive is compatible with the material of the plurality of needles 18 and the material of the plurality of needle posts 40. The plurality of needle posts 40 each include an extending portion 42 that aids in operation of the needle assembly 2 as described below.

Figure 8:
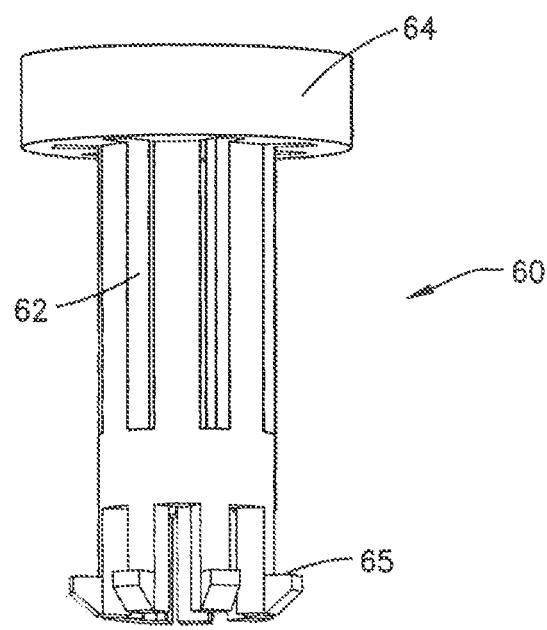
FIG. 8 illustrates a perspective view of a needle guide top.

According to one embodiment, the plurality of needle posts 40 is disposed in a needle guide top 60 as illustrated in FIG. 8. The needle guide top 60 includes a plurality of needle guide slots 62. When each of the plurality of needle posts 40 is assembled into the needle guide top 60, each of the extending portions 42 is disposed and extends through a respective needle guide slot 62. In other words, the needle guide top 60 arranges the plurality of needle posts 40 such that the extending portions 42 extend outward from a centerline of the needle guide top 60 (i.e. the extending portions 42 are each radially aligned with respect to the centerline of the needle guide top 60). Accordingly, the needle posts 40 are able to slide axially through the needle guide slots 62 and within the needle guide top 60 without obstruction. Moreover, the needle guide slots 62 engage the extending portions 42 of the needle posts 40 and prevent the needle posts 40 from rotating.

During assembly and prior to operation, an upper portion 64 of the needle guide top 60 snaps into engagement with the spike housing 8. Specifically, snaps on the distal end of the spike housing 8 axially retain the needle guide top 60 while compressing the upper septum 72. The snaps allow for assembly but lock in place when the needle guide top 60 and the spike housing 8 are pulled apart from one another. The lower septum 76 is disposed in a recess in the upper portion 64 of the needle guide top 60. A lower portion 65 of the needle guide top 60 is also secured as described below.

Figure 12:
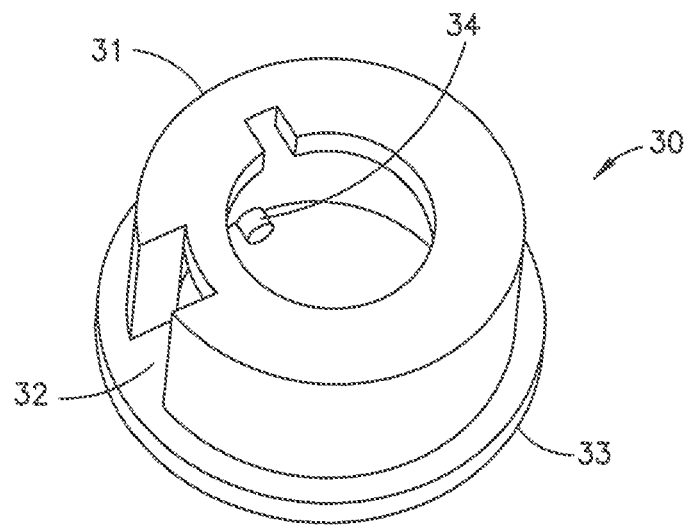
FIG. 12 illustrates a perspective view of a selection ring insert.

The needle assembly 2 further includes a selection ring insert 30 that rotates during operation to identify which needle of the plurality of needles 18 is to be selected. According to one embodiment, as illustrated in FIG. 12, the selection ring insert 30 includes an outer cylindrical surface 31 at a first diameter, a bottom surface 33 at a second diameter and a generally hollow interior. The first diameter is smaller than the second diameter. The selection ring insert 30 also includes a notch 32 and a follower 34. The notch 32 is provided on the outer cylindrical surface 31 of the selection ring insert 30 to engage a selection ring 36. The follower 34 is a protrusion at an interior of the selection ring insert 30 that guides the rotation of the selection ring insert 30. Operation of the notch 32 and the follower 34 are described below.

Figure 11:
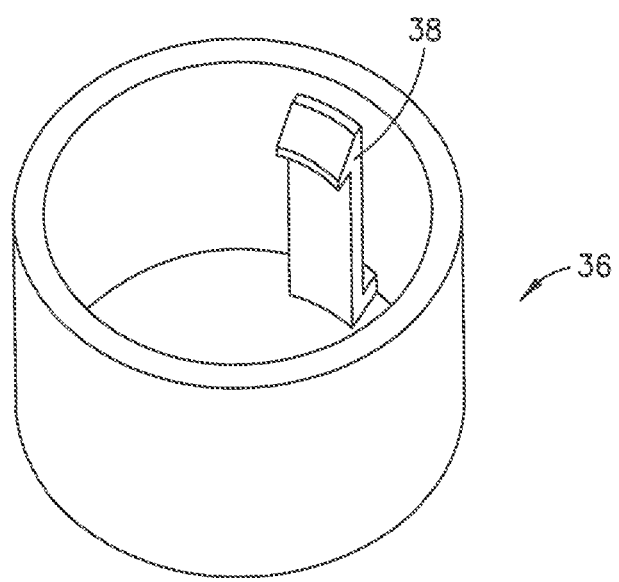
FIG. 11 illustrates a perspective view of a selection ring.

The selection ring 36, according to one embodiment illustrated in FIGS. 3 and 11, is disposed over the outer cylindrical surface 31 of the selection ring insert 30. The selection ring 36 includes a selection ring flange 38 and a chamfer. The selection ring flange 38 is disposed in the notch 32 of the selection ring insert 30 for engagement. Thus, the selection ring insert 30 and the selection ring 36 rotate together. The chamfer allows the selection ring flange 38 of the selection ring 36 to elastically deflect in a radial direction and snap over the needle post 40 of the selected needle 24 when the needle assembly 2 travels from the second position to the first position. During assembly, the selection ring 36 contacts an inner wall 12 of the housing 10. In operation, the selection ring flange 38 contacts the extending portion 42 of the needle post 40 and applies a force to expose a selected needle. The selection ring 36 rotates with respect to the housing 10 but moves axially with the housing 10.

Figure 13:
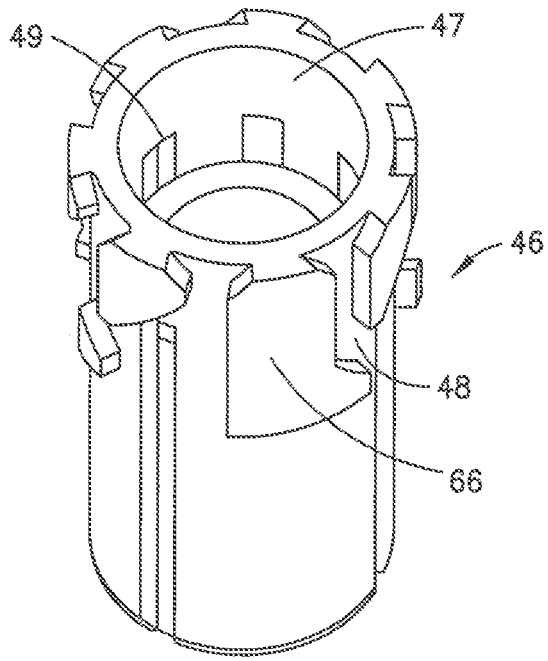
FIG. 13 illustrates a perspective view of a needle guide.

According to one embodiment as illustrated in FIG. 13, the needle assembly 2 also includes a needle guide 46. The needle guide 46 includes an inner cavity 47 that supports a bottom portion of the needle guide top 60 and the sealing septum 50 of the needle assembly 2. During assembly, the needle guide 46 includes recesses 49 along an inner surface of the inner cavity 47 to engage the lower portion 65 of the needle guide top 60.

The needle guide 46 also includes a plurality of curvilinear paths 48 disposed along an outer surface of the needle guide 46. The curvilinear paths 48 comprise a variety of protruded surfaces including a large protruded surface 66 along the outer surface of the needle guide 46. The variety of protruded surfaces of the curvilinear paths 48 create an inscribed passageway to engage the follower 34 of the selection ring insert 30.

According to an alternate embodiment, the follower 34 is disposed on the outer surface of the needle guide 46 and the curvilinear paths 48 are disposed on the interior of the selection ring insert 30. Moreover, a variety of configurations such as tracks and slides are contemplated.

The needle assembly 2, according to one embodiment, further includes a cap 54 secured to the housing 10. The cap 54 and the housing 10 support all of the components of the needle assembly 2. In assembly, the cap 54 engages the housing 10 via a snap-fit joint, for example, and contacts a bottom wall of the housing 10. The cap 54 also includes a hole 55 at its distal end allowing the needle guide 46 to enter into. The hole 55 is sized to prevent the needle guide 46 from exiting the cap 54 and to minimize unauthorized tampering.

Figure 6:
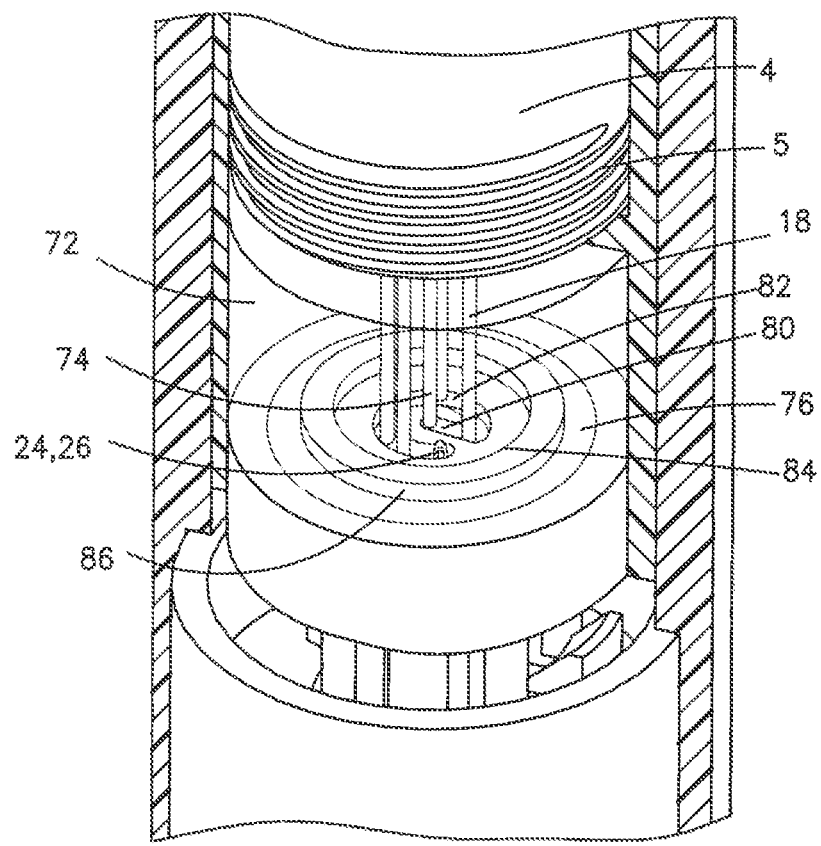
FIG. 6 illustrates a partial cross sectional view of the communication septum in the second position.
Figure 7:
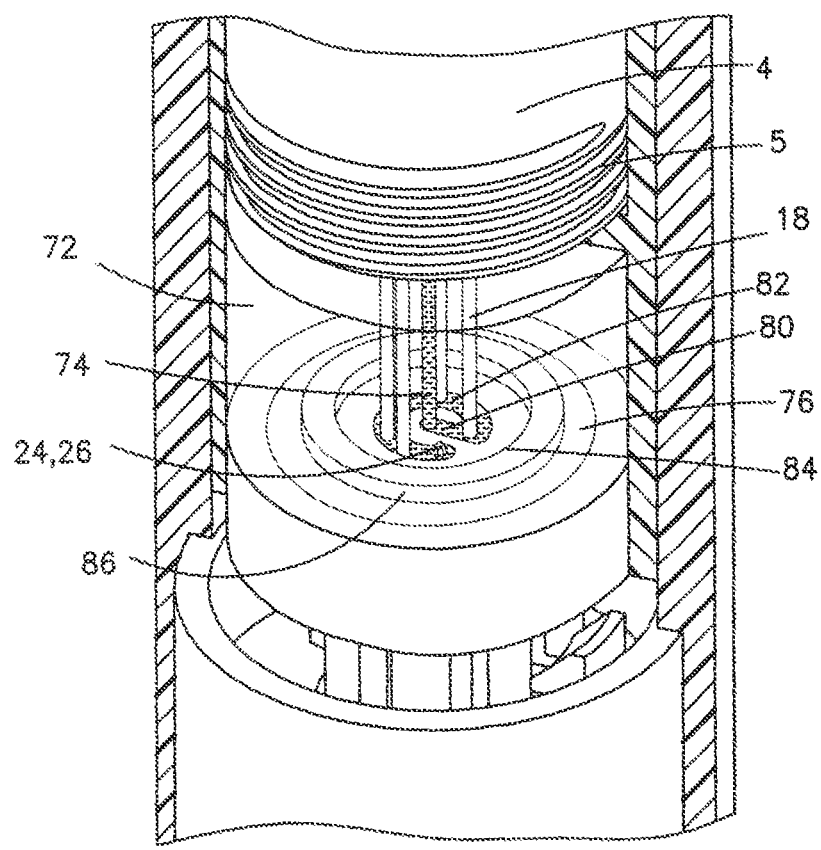
FIG. 7 illustrates a partial cross sectional view of the communication septum filled with medicament in the second position.

According to one embodiment, FIGS. 5-7 illustrate the housing 10 in the second position where a selected needle 24 amongst the plurality of needles 18 is exposed for medicament delivery. Specifically, the selection ring 36 moves downward with the housing 10. At the same time, the selection ring flange 38 contacts a top surface of the extending portion 42 of the needle post 40 to move the selected needle 24 downward along the respective needle guide slot 62. Accordingly, as described above, the proximal end 26 of the selected needle 24 enters into fluid communication with the septum chamber and a sharpened distal end 28 of the selected needle 24 pierces the sealing septum 50 and is exposed.

FIG. 6 illustrate the proximal end 26 of the selected needle 24 in fluid communication with the circular cavity 82 of the septum chamber. Each of the plurality of needles 18 is aligned and configured to be in fluid communication with the septum chamber when selected by the selection ring 36.

FIG. 7 illustrates the medicament from the medication delivery pen 4 entering through the upper septum hole 74 and traveling in the longitudinal and circular cavities 80, 82 of the septum chamber. Accordingly, in the second position of the needle assembly 2, the proximal end 26 of the selected needle 24 receives the medicament. The medicament travels through the selected needle 24 and medicament delivery is administered at the sharpened distal end 28 of the selected needle 24.

Figure 14:
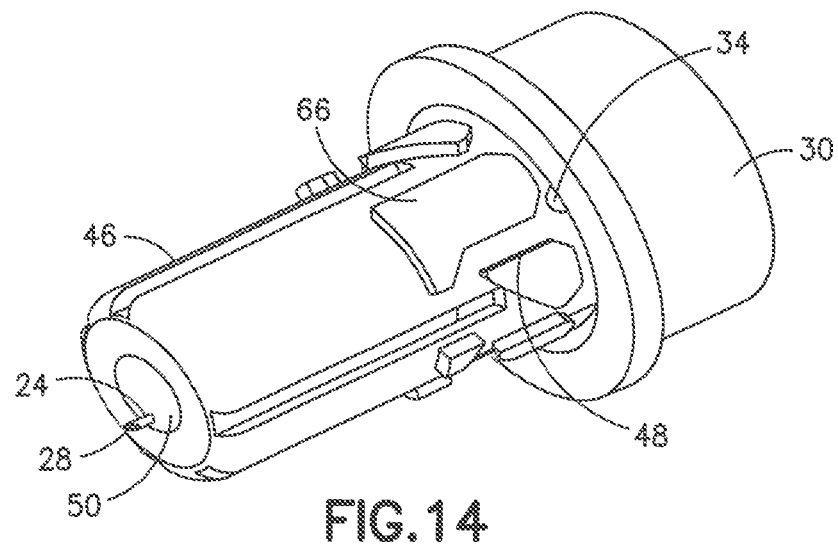
FIG. 14 illustrates a perspective view of the selection ring insert and the needle guide beginning to leave the first position.

FIGS. 14-18 illustrate a subassembly of the needle guide 46 and the selection ring insert 30 that show the various steps of moving between the first and second positions. Specifically, FIG. 14 illustrates the selection ring insert 30 and the needle guide 46 beginning to move from the first position. The follower 34 of the selection ring insert 30 is not engaged to the curvilinear path 48 of the needle guide 46. As the needle assembly 2 leaves the first position, the selected needle 24 begins to pierce the sealing septum 50 and the remaining plurality of needles 18 are all sealed and sterilized in the sealing septum 50 of the needle assembly 2.

Figure 15:
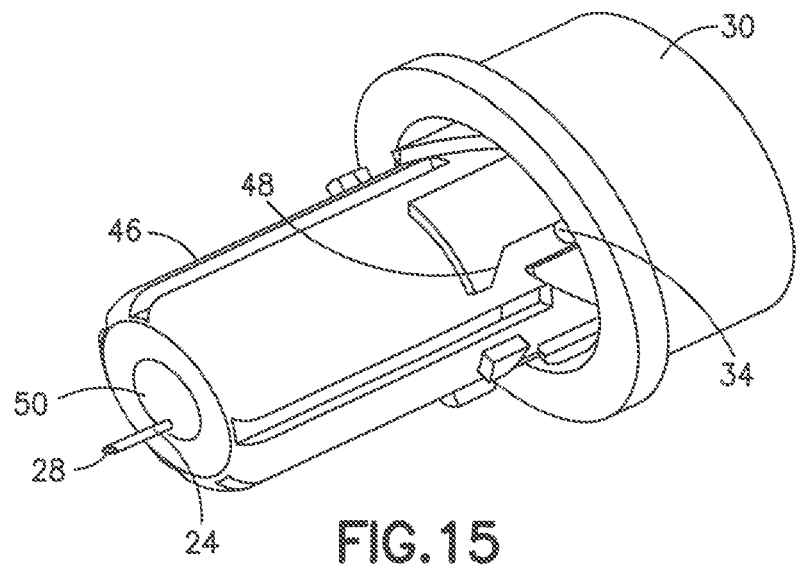
FIG. 15 illustrates a perspective view of the selection ring insert and the needle guide where the selection ring insert is traveling toward the second position from the first position.

As the user pulls the housing 10 from the first position, FIG. 15 illustrates the follower 34 of the selection ring insert 30 entering into the curvilinear path 48 of the needle guide 46. The curvilinear path 48 gradually causes the selection ring insert 30 to rotate with respect to the needle guide 46 and the housing 10. The inner housing wall 12 of the housing 10 contacts the selection ring 36 and causes the selection ring insert 30 to axially move with the housing 10. When the selection ring insert 30 axially moves toward the second position, the selection ring insert 30 also rotates as the follower 34 travels along the curvilinear path 48 of the needle guide. Since the selection ring 36 is rotationally coupled to the selection ring insert 30, the flange 38 of the selection ring 36 pulls the extending portion 42 of the needle post 40 of the selected needle 24 causing the distal end 28 of the selected needle 24 to pierce the sealing septum 50 of the needle assembly 2 and expose the selected needle 24 for medication delivery.

Figure 16:
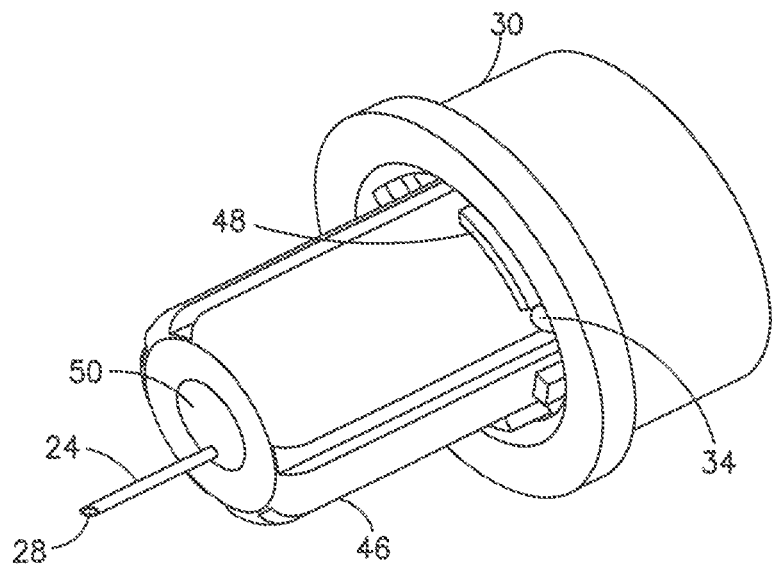
FIG. 16 illustrates a perspective view of the selection ring insert and the needle guide in the second position.

FIG. 16 illustrates the subassembly in the second position when the user pulls the housing 10 away from the medication delivery pen 4. Specifically, the follower 34 is at the end of the curvilinear path 48. In this position, as illustrated in FIGS. 5-7, the distal end 28 of the selected needle 24 pierces the sealing septum 50 of the needle assembly 2 in a fully extended state and the needle assembly 2 is ready for medication delivery. The proximal end 26 of the selected needle 24 enters into fluid communication with the septum chamber as described above to administer the medication.

The proximal end 20 of the remaining needles 18 continues to be disposed in the upper septum 72. The distal end 22 of the remaining needles 18 also continues to stay sealed and sterilized in the sealing septum 50 of the needle assembly 2.

During operation, although the selected needle 24 moves axially, the selected needle 24 does not move radially. In fact, none of the plurality of needles 18 substantially moves radially or rotates at any point during operation. No substantial radial or rotational movement in this regard is understood as 0±5% with respect to a centerline of the needle assembly 2. Preferably, one skilled in the art understands that substantial in this context means that no radial or rotational movement is required to perform the intended function. However, slight radial or rotational movement may be desired to ensure the proper spacing of parts for smooth operation and proper movement of the plurality of needles 18 axially without jamming. This configuration improves simplicity of the design and reduces movement of parts in the needle assembly 2.

The user cannot draw the housing 10 out from the needle assembly 2 any further than the second position of the needle assembly 2 because of the configuration illustrated in FIG. 5. Specifically, the housing flanges 14 engage with spike housing 8 and prevent further axial movement of the needle assembly 2. The cap 54 and the needle guide 46 also contact a patient delivery site during needle insertion and injection to restrict further axial movement.

Figure 17:
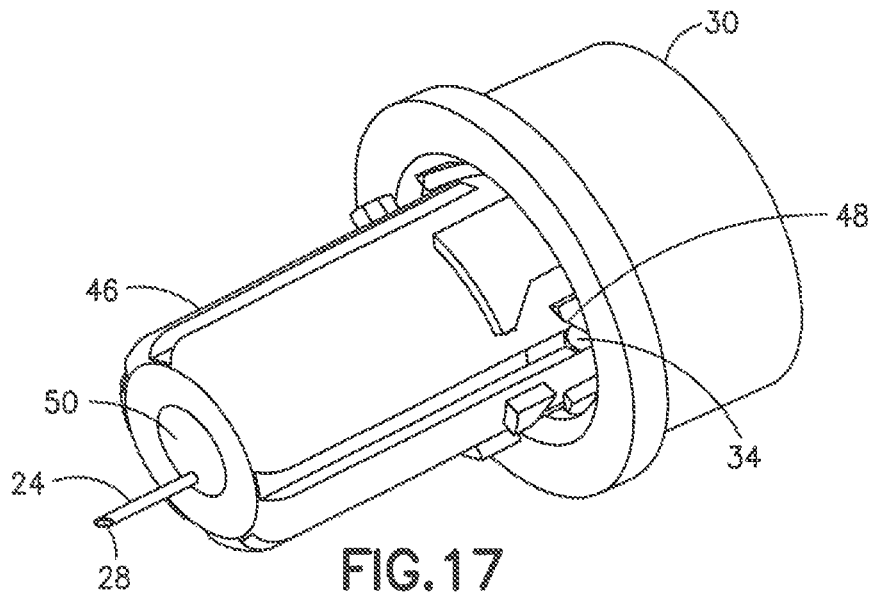
FIG. 17 illustrates a perspective view of the selection ring insert and the needle guide where the selection ring insert is traveling toward the first position from the second position.

FIG. 17 illustrates the subassembly returning from the second position back to the first position when the user pushes the housing 10 back toward the medication delivery pen 4. The cap 54 pushes the selection ring insert 30 upwards which moves the extending portion 42 of the selected needle 24 upward. The distal end 28 of the selected needle 24 returns into the sealing septum 50 of the needle assembly 2. The sealing septum 50 encloses the selected needle 24 and protects the user. Meanwhile, the follower 34 enters into a different curvilinear path 48 so that the selection ring insert 30 continues to rotate and prepare the flange 38 of the selection ring 36 to align with an adjacent needle of the plurality of needles 18 for a subsequent injection. Specifically, the chamfer of the selection ring 36 allows the flange 38 to elastically deflect in a radial direction and snap over the needle post 40 of the adjacent needle of the plurality of needles 18 when the needle assembly 2 travels from the second position to the first position.

Figure 18:
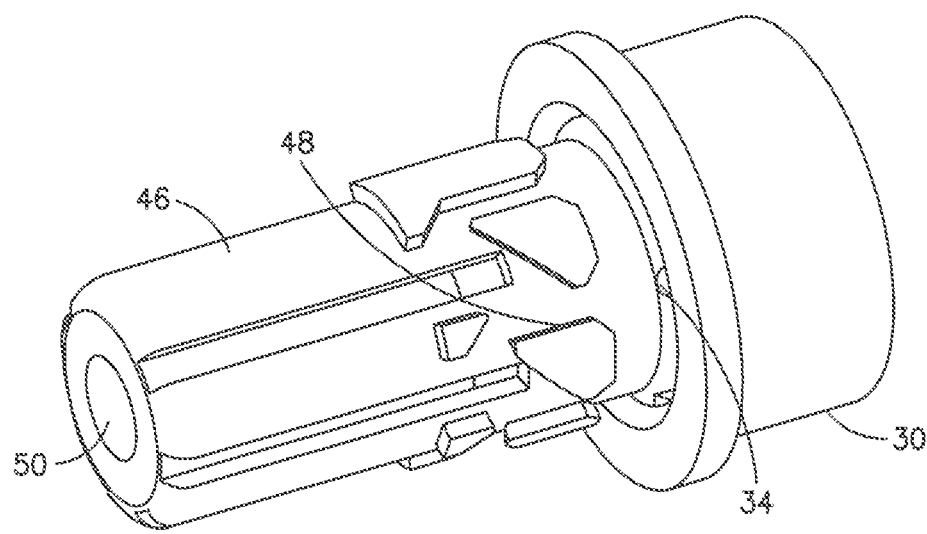
FIG. 18 illustrates a perspective view of the selection ring insert and the needle guide where the selection ring insert returns to the first position.

FIG. 18 illustrates the subassembly after it has returned back to the first position where the distal ends 22 of each of the plurality of needles 18 is retracted and disposed in the sealing septum 50 of the needle assembly 2. The flange 38 of the selection ring 36 is now rotated and aligned to push the extending portion 42 of the needle post 40 of the subsequent needle amongst the plurality of needles 18 when the housing 10 moves from the first position to the second position.

The process of moving from the first position to the second position and back to the first position while rotating the selection ring 36 repeats so that each needle amongst the plurality of needles 18 is individually exposed in a consecutive manner from a first needle, to each adjacent needle and to a last needle. Additionally, as illustrated in FIGS. 13 and 14, the curvilinear path 48 includes a large protruded surface 66 that causes the last needle of the plurality of needles 18 to be continuously selected and reused. In other words, when the selection ring 36 engages the last needle of the plurality of needles 18, the curvilinear path 48 is configured not to rotate the selection ring insert 30 any further. This configuration advantageously provides a means for repeated use of the last needle in the needle assembly 2 after each of the other needles 18 is used only once. This feature is advantageous when a user does not have a new needle assembly 2 immediately available for use.

Figure 19:
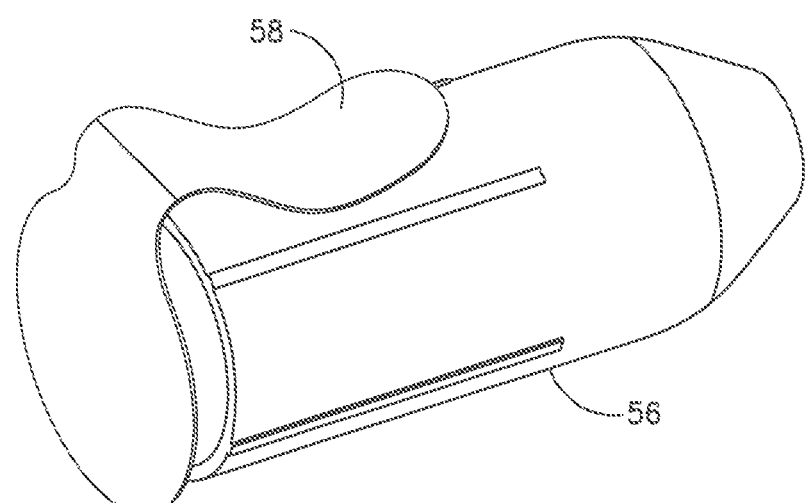
FIG. 19 illustrates a perspective view of the needle assembly in a cover and sealed by a teardrop label.

FIG. 19, according to one embodiment, illustrates a cover 56 that encloses the needle assembly 2. The cover 56 is sealed with a teardrop label 58 to seal the needle assembly 2 and maintain its sterility for transportation and security purposes prior to operating with the medication delivery pen 4. When the needle assembly 2 is ready for use, the user peels off the teardrop label 58 and removes the needle assembly 2 from the cover 56.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An attachable needle assembly for use on a medication delivery pen, the needle assembly comprising:
    a housing enclosing:
        a communication septum of the needle assembly defining a septum chamber;
        a plurality of needles disposed in the communication septum of the needle assembly;
        a selection ring insert that rotates and identifies which needle of the plurality of needles is to be selected; and
        a selection ring that applies a force to expose the selected needle and moves the selected needle to be in fluid communication with the septum chamber of the communication septum of the needle assembly, the selection ring moves with the selection ring insert when the housing moves from a first position to a second position, wherein
    when the housing is in the first position, the plurality of needles is not exposed, and when the housing is in the second position, the selected needle is in fluid communication with the septum chamber of the communication septum of the needle assembly and exposed for medicament delivery.

2. The attachable needle assembly of claim 1, further comprising:
    a spike housing that is configured to engage the medication delivery pen, and configured to pierce a reservoir septum of the medication delivery pen; wherein
    the septum chamber of the needle assembly is in continuous fluid communication with the spike housing;
    the spike housing includes a spike that is configured to pierce the reservoir septum of the medication delivery pen, and
    the spike is in fluid communication with the communication septum of the needle assembly.

3. The attachable needle assembly of claim 2, wherein the communication septum of the needle assembly includes
    an upper septum that maintains needle sterility; and
    a lower septum that provides fluid communication to the spike housing.

4. The attachable needle assembly of claim 2, wherein the plurality of needles do not pierce the reservoir septum of the medication delivery pen.

5. The attachable needle assembly of claim 3, wherein the lower septum includes the septum chamber comprising a circular cavity that carries medicament from the spike housing and fluidly communicates with the selected needle when the housing is in the second position.

6. The attachable needle assembly of claim 3, wherein when the housing is in the first position, a proximal end of each needle of the plurality of needles is disposed in the upper septum and a distal end of each needle of the plurality of needles is disposed in a sealing septum.

7. The attachable needle assembly of claim 3, wherein when the housing is in the second position, a proximal end of the selected needle is disposed in the lower septum.

8. The attachable needle assembly of claim 3, wherein when the housing is in the second position, a proximal end of each of a remaining plurality of needles is disposed in the upper septum.

9. The attachable needle assembly of claim 1, wherein
    each of the plurality of needles is secured to a respective needle post of a plurality of needle posts; and
    the selection ring includes a flange that contacts one of the plurality of needle posts to expose a distal end of the selected needle when the housing is in the second position.

10. The attachable needle assembly of claim 9, further comprising
    a needle guide top that houses the plurality of needle posts; and
    the plurality of needle posts each include an extending portion, wherein
    the needle guide top arranges the plurality of needle posts such that the extending portions extend outward from a centerline of the needle guide top.

11. The attachable needle assembly of claim 1, further comprising
    a sealing septum of the needle assembly that seals and maintains sterility of the plurality of needles, wherein
    when the housing is in the first position, a distal end of each of the plurality of needles is disposed in the sealing septum of the needle assembly.

12. The attachable needle assembly of claim 11, wherein when the housing is in the second position, a distal end of each of a remaining plurality of needles is disposed in the sealing septum of the needle assembly.

13. The attachable needle assembly of claim 11, wherein when the housing is in the second position, a distal end of the selected needle of the plurality of needles pierces the sealing septum of the needle assembly and is exposed.

14. The attachable needle assembly of claim 1, wherein the plurality of needles includes at least seven needles.

15. The attachable needle assembly of claim 1, wherein the plurality of needles only move axially, do not substantially move radially and do not substantially rotate.

16. The attachable needle assembly of claim 1, further including
    a cover enclosing the needle assembly; and
    a label sealing and maintaining sterility of the needle assembly in the cover prior to operating with the medication delivery pen.

17. The attachable needle assembly of claim 1, wherein the selection ring is in contact with the selection ring insert.

18. The attachable needle assembly of claim 1, wherein the selection ring and the selection ring insert are unexposed to an exterior of the housing.

19. The attachable needle assembly of claim 1, wherein rotation of the selection ring insert causes the selection ring to simultaneously rotate.

20. An attachable needle assembly for use on a medication delivery pen, the needle assembly comprising:
    a housing enclosing:
        a communication septum of the needle assembly defining a septum chamber;
        a plurality of needles disposed in the communication septum of the needle assembly,
        a selection ring insert that rotates and identifies which needle of the plurality of needles is to be selected, and
        a selection ring that applies a force to expose the selected needle and moves the selected needle to be in fluid communication with the septum chamber of the communication septum of the needle assembly, wherein each of the plurality of needles is secured to a respective needle post of a plurality of needle posts;

the selection ring includes a flange that contacts one of the plurality of needle posts to expose a distal end of the selected needle expose a distal end of the selected needle; and the selection ring insert includes a notch that mates with the flange of the selection ring.

21. An attachable needle assembly for use on a medication delivery pen, the needle assembly comprising:
a housing enclosing:
a communication septum of the needle assembly defining a septum chamber;
a plurality of needles disposed in the communication septum of the needle assembly;
a selection ring insert that rotates and identifies which needle of the plurality of needles is to be selected; and
a selection ring that applies a force to expose the selected needle and moves the selected needle to be in fluid communication with the septum chamber of the communication septum of the needle assembly, wherein
when the housing is in a first position, the plurality of needles is not exposed, and when the housing is in a second position, the selected needle is in fluid communication with the septum chamber of the communication septum of the needle assembly and exposed for medicament delivery; and
the selection ring insert rotates with respect to the housing and moves axially with the housing when the housing travels between the first position and the second position.

22. An attachable needle assembly for use on a medication delivery pen, the needle assembly comprising:
a housing enclosing:
a communication septum of the needle assembly defining a septum chamber;
a plurality of needles disposed in the communication septum of the needle assembly;
a selection ring insert that rotates and identifies which needle of the plurality of needles is to be selected; and
a selection ring that applies a force to expose the selected needle and moves the selected needle to be in fluid communication with the septum chamber of the communication septum of the needle assembly, wherein
when the housing is in a first position, the plurality of needles is not exposed, and when the housing is in a second position, the selected needle is in fluid communication with the septum chamber of the communication septum of the needle assembly and exposed for medicament delivery;
the selection ring insert includes a follower comprising a protrusion;
the plurality of needles are disposed in a needle guide, the needle guide having a curvilinear path; and
the follower travels along the curvilinear path to rotate the selection ring insert.

23. The attachable needle assembly of claim 22, wherein the curvilinear path rotates the selection ring insert to select each needle consecutively from a first needle to a last needle of the plurality of needles.

24. The attachable needle assembly of claim 22, wherein the curvilinear path is configured to cause the selection ring insert to select and continuously reuse a last needle of the plurality of needles.

25. An attachable needle assembly for use on a medication delivery pen, the needle assembly comprising:
a housing enclosing:
a communication septum of the needle assembly defining a septum chamber;
a plurality of needles disposed in the communication septum of the needle assembly;
a selection ring insert that rotates and identifies which needle of the plurality of needles is to be selected; and
a selection ring that applies a force to expose the selected needle and moves the selected needle to be in fluid communication with the septum chamber of the communication septum of the needle assembly; and
a cap connected to the housing that applies a force to the selection ring insert when the housing is moving from a second position to a first position; wherein
when the housing is in the first position, the plurality of needles is not exposed, and when the housing is in the second position, the selected needle is in fluid communication with the septum chamber of the communication septum of the needle assembly and exposed for medicament delivery.

26. A method of operating an attachable needle assembly on a medication delivery pen, the method comprising:
disposing a plurality of needles in a communication septum of a housing of the needle assembly;
rotating a selection ring insert to identify which needle of the plurality of needles is to be selected, the selection ring insert rotates with respect to the housing; and
applying a force, by a selection ring, to the selected needle to expose the selected needle and to move the selected needle to be in fluid communication with a septum chamber of the communication septum of the needle assembly, wherein
when the housing is in a first position, the plurality of needles is not exposed, and when the housing is in a second position, the selected needle of the plurality of needles is in fluid communication with the septum chamber of the communication septum of the needle assembly and exposed for medicament delivery; and
the selection ring insert moves axially with the housing when the housing travels between the first position and the second position.

* * * * *

UNITED STATES PATENT AND TRADEMARK OFFICE
CERTIFICATE OF CORRECTION

PATENT NO.         : 11,071,833 B2
APPLICATION NO.    : 16/094809
DATED              : July 27, 2021
INVENTOR(S)        : Sudarsan Srinivasan et al.

Page 1 of 1

It is certified that error appears in the above-identified patent and that said Letters Patent is hereby corrected as shown below:

In the Claims

Claim 20, Column 11, Lines 8-9, "selected needle expose a distal end of the selected needle; and" should read --selected needle; and--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*